United States Patent [19]

Thyes et al.

[11] Patent Number: 4,845,302
[45] Date of Patent: Jul. 4, 1989

[54] PREPARATION OF 5H-DIBENZO[A,D]CYCLOHEPTEN-5-ONES

[75] Inventors: Marco Thyes, Ludwigshafen; Gerd Steiner, Kirchheim, both of Fed. Rep. of Germany

[73] Assignee: BASF Aktiengesellschaft, Ludwigshafen, Fed. Rep. of Germany

[21] Appl. No.: 134,885

[22] Filed: Dec. 18, 1987

[30] Foreign Application Priority Data

Dec. 24, 1986 [DE] Fed. Rep. of Germany ....... 3644462

[51] Int. Cl.$^4$ .............................................. C07C 45/46
[52] U.S. Cl. ................... 568/323; 568/322; 562/840
[58] Field of Search ............... 568/322, 323; 260/544 B

[56] References Cited

PUBLICATIONS

Sethua et al. Friedel–Crafts & Related Reactions, vol. III, pp. 911–915 & 1058–1070 (1964).
Dibenztroponeacetic and -propionic Acids... Dunn et al., J. Med. Chem., 1977 vol. 20, No. 12, pp. 1557–1562.
Dibenzotropone-and Dibenzosuberonecarboxylic Acids... Dunn et al., J. Med. Chem. 1979, vol. 22, No. 11, pp. 1357–1363.
Chem. Ber. 84 (1951), pp. 671–679.
1-Methylene-2,3,6,7-Dibenzcycloheptatriene, COPE et al., J. Amer. Chem. Soc. 73 (Apr. 1951), pp. 1673–1678.

Primary Examiner—James H. Reamer
Attorney, Agent, or Firm—Keil & Weinkauf

[57] ABSTRACT

5H-Dibenzo[a,d]cyclohepten-5-ones (I)

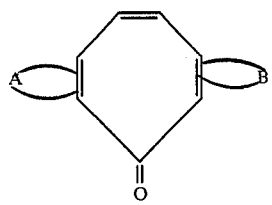

(A and B being radicals for completing aromatic ring systems) are prepared by converting (Z)-2-(2-arylethenyl)arylcarboxylic acids (II)

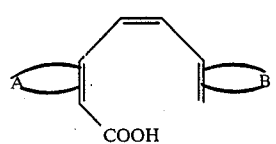

or E/Z-isomer mixtures thereof with a halogenating agent for carboxylic acids at from ($-30°$) to $+120°$ C. to the corresponding carbonyl halides (III)

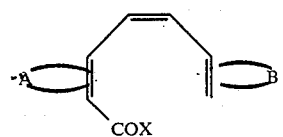

where X is halogen, and cyclizing said carbonyl halides at from 0° to 100° C. in the presence of a Lewis acid.

8 Claims, No Drawings

PREPARATION OF 5H-DIBENZO[A,D]CYCLOHEPTEN-5-ONES

The present invention relates to a novel process for preparing 5H-dibenzo[a.d]cyclohepten-5-ones of the general formula I

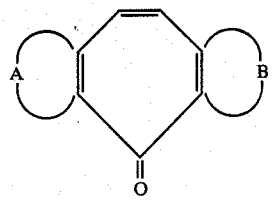
(I)

where A and B are each radicals for completing aromatic ring systems.

J. Med. Chem. 20 (1977), 1557 discloses that the direct cyclization of (E/Z)-2-(2-m-tolylethenyl)benzoic acid (E/Z ratio=1:1) leads not to a tricyclic ketone of type I, but to a 6-ring lactone

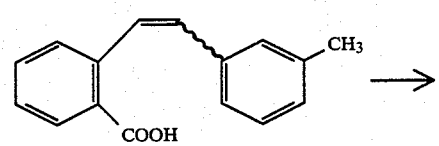

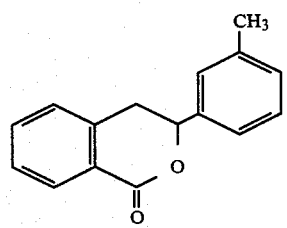

It has further been disclosed that compounds of the type I are preparable by hydrogenating the ethenyl double bond in E/Z compounds II'

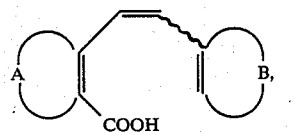
(II')

cyclizing, and subsequently reintroducing the previously removed double bond [eg. J. Med. Chem. 20 (1977), 1557; J. Med. Chem. 22 (1979), 1357; Chem. Ber. 84 (1951), 671; or J. Amer. Chem. Soc. 73 (1951), 1673].

It is an object of the present invention to develop a process for getting to the 5H-dibenzo[a,d]cyclohepten-5-ones I by a shorter route.

We have found that this object is achieved with a process for preparing a 5H-dibenzo[a,d]cyclohepten-5-one of the general formula I

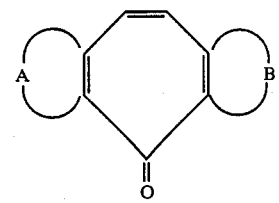
(I)

where the radicals A and B are each radicals for completing an aromatic ring system, which comprises converting a (Z)-2-(2-arylethenyl)arylcarboxylic acid of the general formula II

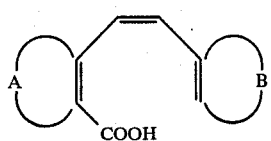
(II)

at from (−30°) to +120° C. with a halogenating agent for carboxylic acids into the corresponding carbonyl halide of the general formula III

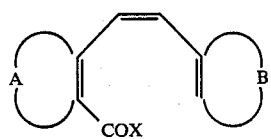
(III)

where X is halogen, and cyclizing the said carbonyl halide at from 0° to 100° C. in the presence of a Lewis acid.

The rings containing A and B correspond to benzene and fused benzenes such as 1,2-naphthalene, 2,3-naphthalene and up to triply substituted derivatives thereof.

Possible substituents are:

halogen, such as fluorine, chlorine or bromine, in particular fluorine or chlorine, trifluoromethyl, $C_1$-$C_8$-alkyl, in particular $C_1$-$C_4$-alkyl, such as methyl, ethyl, n-propyl, isopropyl, n-butyl, isobutyl, sec-butyl or tert-butyl, $C_1$-$C_8$-alkoxy, in particular $C_1$-$C_4$-alkoxy such as methoxy, ethoxy, n-propoxy, isopropoxy, n-butoxy, isobutoxy, sec-butoxy or tert-butoxy.

Preferably, the substituents are present on the ring containing the group B.

Specific examples of preferred starting compounds II are those which correspond to the following preferred products:

5H-dibenzo[a,d]cyclohepten-5-one;
1-chloro-5H-dibenzo[a,d]cyclohepten-5-one;
2-chloro-5H-dibenzo[a,d]cyclohepten-5-one;
3-chloro-5H-dibenzo[a,d]cyclohepten-5-one;
1-bromo-5H-dibenzo[a,d]cyclohepten-5-one;
3-bromo-5H-dibenzo[a,d]cyclohepten-5-one;
1-fluoro-5H-dibenzo[a,d]cyclohepten-5-one;
2-fluoro-5H-dibenzo[a,d]cyclohepten-5-one;
3-fluoro-5H-dibenzo[a,d]cyclohepten-5-one;
1,2-dichloro-5H-dibenzo[a,d]cyclohepten-5-one;
1,4-dichloro-5H-dibenzo[a,d]cyclohepten-5-one;
2,3-dichloro-5H-dibenzo[a,d]cyclohepten-5-one;
2,4-dichloro-5H-dibenzo[a,d]cyclohepten-5-one;
1,2-dibromo-5H-dibenzo[a,d]cyclohepten-5-one;

2,3-dibromo-5H-dibenzo[a,d]cyclohepten-5-one;
2-trifluoromethyl-5H-dibenzo[a,d]cyclohepten-5-one;
1-methyl-5H-dibenzo[a,d]cyclohepten-5-one;
2-methyl-5H-dibenzo[a,d]cyclohepten-5-one;
3-methyl-5H-dibenzo[a,d]cyclohepten-5-one;
1-ethyl-5H-dibenzo[a,d]cyclohepten-5-one;
2-ethyl-5H-dibenzo[a,d]cyclohepten-5-one;
3-ethyl-5H-dibenzo[a,d]cyclohepten-5-one;
2-propyl-5H-dibenzo[a,d]cyclohepten-5-one;
2-isopropyl-5H-dibenzo[a,d]cyclohepten-5-one;
2-butyl-5H-dibenzo[a,d]cyclohepten-5-one;
1,2-dimethyl-5H-dibenzo[a,d]cyclohepten-5-one;
2,3-dimethyl-5H-dibenzo[a,d]cyclohepten-5-one;
2,4-dimethyl-5H-dibenzo[a,d]cyclohepten-5-one;
1-methoxy-5H-dibenzo[a,d]cyclohepten-5-one;
2-methoxy-5H-dibenzo[a,d]cyclohepten-5-one;
3-methoxy-5H-dibenzo[a,d]cyclohepten-5-one;
1-ethoxy-5H-dibenzo[a,d]cyclohepten-5-one;
2-ethoxy-5H-dibenzo[a,d]cyclohepten-5-one;
3-ethoxy-5H-dibenzo[a,d]cyclohepten-5-one;
1,2-dimethoxy-5H-dibenzo[a,d]cyclohepten-5-one;
2,3-dimethoxy-5H-dibenzo[a,d]cyclohepten-5-one;
1,4-dimethoxy-5H-dibenzo[a,d]cyclohepten-5-one.

Some of the (Z)-2-(2-arylethenyl)arylcarboxylic acids II are known (eg. J. Org. Chem. 43 (1978), 3283), while the others can be prepared by known methods using the Wettig reaction. The Z-isomer may be isolated from the E/Z mixtures by crystallization or chromatography.

It is also possible to use E/Z-isomer mixtures, in particular those having a high Z-isomer content. If an E/Z-isomer mixture is present, it can be advantageous to carry along the E-isomer through the reaction stages, since, in general, it leads to more easily isolable end products and, in addition, has no hindering effect on the reaction of the Z-isomer.

In what follows, the process according to the invention is described in terms of the Z-isomer, although it is equally applicable to the E/Z mixture.

Preparation of carbonyl halides III

In an inert solvent, a (Z)-2-(2-arylethenyl)arylcarboxylic acid II is introduced initially, with or without an acid binding agent, and reacted at from (−30°) to +120° C., preferably at from 20° to 80° C., by dropwise addition of a halogenating agent for carboxylic acids.

A suitable acid-binding agent is for example an organic base such as triethylamine or pyridine. If an acid-binding agent is present, it is advantageous to isolate the product III. If the crude carbonyl halide III is to be used directly, it is preferable not to employ an acid-binding agent.

Preferred halogenating agents for carboxylic acids are thionyl chloride, thionyl bromide, phosphorus oxychloride, phosphorus trichloride, phosphorus pentachloride, phosphorus tribromide and phosphorus pentabromide. Particular preference is given to thionyl chloride.

Preferably, the halogenating agent for carboxylic acids is used in an equimolar amount or an excess, preferably of up to 3 equivalents of II. Particular preference is given to using the halogenating agent for the carboxylic acid in an equimolar amount or in an excess of up to 5 mol %. This is advisable in particular if the crude carbonyl halide III is to be used directly.

Suitable solvents are for example halogenated hydrocarbons such as methylene chloride, chloroform, ethylene chloride, 1,1,1-trichloroethane, 1,1,2,2-tetrachloroethane, chlorobenzene and bromobenzene or aromatic hydrocarbons such as benzene, toluene and the xylenes. Preference is given to methylene chloride, in particular if the halogenation product is to be used directly.

Preparation of 5H-dibenzo[a,d]cyclohepten-5-ones I

The carbonyl halide III is preferably introduced initially in a solvent inert under Friedel-Crafts acylation, for example a chlorohydrocarbon, eg. methylene chloride, ethylene chloride, 1,1,1-trichloroethane or 1,1,2,2-tetrachloroethane, preferably methylene chloride, and reacted at from 0° to 100° C., preferably at from 10° to 80° C., particularly preferably at from 20° to 30° C., by addition of a solid Lewis acid a little at a time or by dropwise addition of a suspension or slurry of a Lewis acid in one of the inert solvents.

Suitable Lewis acids are of the usual kind, with preference being given to aluminum trichloride.

The Lewis acid is preferably used in an equimolar amount or in excess, preferably in an amount from 1.2 to 1.5 moles per mole of III.

In a preferred method of isolating the 5H-dibenzo[a,d]cyclohepten-5-one I, the hydrolysis mixture has added to it, for the purpose of reducing the solubility of the dibenzocycloheptenone in the organic phase, an apolar, organic solvent, for example petroleum ether having a boiling range from 40° to 60° C. or cyclohexane, and the dibenzocycloheptenone is then separated off by filtration. The amount of apolar, organic solvent used therein can have been selected for example in such a way that the volume ratio between the solvent used for the reaction and this apolar organic solvent ranges from about 0.2:1 to 0.6:1.

The compounds I serve as intermediates for preparing pharmacologically active 5-cyanomethylene-5H-dibenzo[a,d]cycloheptenes (German Laid-Open Application DOS No. 3,009,034). (Z)-[2-Chloro-10-(4-methyl-1-piperazinyl)-5H-dibenzo[a,d]cyclohepten-5-ylidene]acetonitrile (mp. 229°–231° C.) was obtainable via the intermediates 2-chloro-10,11-dibromo-10,11-dihydro-5H-dibenzo[a,d]cyclohepten-5-one (prepared by addition of bromine onto the olfinic double bond of 2-chloro-5H-dibenzo[a,d]cyclohepten-5-one; mp. 161°–164° C.), the mixture of 10-bromo-2-chloro-5H-dibenzo[a,d]cyclohepten-5-one and 11-bromo-2-chloro-5H-dibenzo[a,d]cyclohepten-5-one in a ratio of 15:85 (mp. 134°–137° C.), and a mixture of (E/Z)-[10-bromo-2-chloro-5H-dibenzo[a,d]cyclohepten-5-ylidene]acetonitrile and (E/Z)-[11-bromo-2-chloro-5H-dibenzo[a,d]cyclohepten-5-ylidene]acetonitrile (mp. 97°–100° C.). Furthermore, the pharmacologically active mixture of (E/Z)-[2-fluoro-10-(4-methyl-1-piperazinyl)-5H-dibenzo[a,d]cyclohepten-5-ylidene]acetonitrile (hemihydrates) and (E/Z)-[2-fluoro-11-(4-methyl-1-piperazinyl)-5H-dibenzo[a,d]cyclohepten-5-ylidene]acetonitrile (hemihydrates) (mp. 98°–101° C.) was obtainable via 2-fluoro-5H-dibenzo[a,d]cyclohepten-5-one, the pharmacologically active mixture of (E/Z)-[1-chloro-10-(4-methyl-1-piperazinyl)-5H-dibenzo[a,d]cyclohepten-5-ylidene]acetonitrile and (E/Z)-[1-chloro-11-(4-methyl-1-piperazinyl)-5H-dibenzo[a,d]cyclohepten-5-ylidene]acetonitrile (mp. 101°–104° C. via 1-chloro-5H-dibenzo[a,d]cyclohepten-5-one, and the pharmacologically active mixture of (E/Z)-[3-chloro-10-(4-methyl-1-piperazinyl)-5H-dibenzo[a,d]-cyclohepten-5-ylidene]acetonitrile and (E/Z)-[3-chloro-11-(4-methyl-1-piperazinyl)-5H-dibenzo[a,d]cyclohepten-5- ylidene]acetonitrile (mp. 102°–105° (.) via 3-chloro-5H-dibenzo[a,d]cyclohepten-5-one.

EXAMPLE 1

2-Chloro-5H-dibenzo[a,d]cyclohepten-5-one

To 500 g (1.933 mol) of (E/Z)-2-[2-(3-chlorophenylethenyl]benzoic acid (in a ratio of about 23:77) in 500 ml of methylene chloride were added dropwise with stirring at the reflux temperature 241.6 g (2.031 mol) of thionyl chloride in the course of 1 hour and stirred in for 1 hour. Thereafter a suspension of 333 g (2.497 mol) of anhydrous aluminum chloride in 100 ml of methylene chloride was added at room temperature in the course of 45 min and stirred in at room temperature for 30 min, and the reaction mixture was then poured with stirring onto a mixture of 3 kg of ice and 1 l of water. The hydrolysis mixture was stirred for about 30 min. 1 l of petroleum ether (boiling range from 40° to 60° C.) was then added with stirring. The mixture was stirred for a further 30 min and then filtered with suction. The filter residue was washed first with 5 l of water and then with 1 l of petroleum ether (boiling range from 40° to 60° C.) and dried. 270 g were isolated of 2-chloro-5H-dibenzo-[a,d]cyclohepten-5-one in 58% yield; melting point 160°–161° C.

EXAMPLE 2

2-Fluoro-5H-dibenzo[a,d]cyclohepten-5-one

To 18.2 g (75.1 mmol) of (E/Z)-2-[2-(3-fluorophenyl)ethenyl]benzoic acid (in a ratio of about 27:73) in 50 ml of methylene chloride were added dropwise with stirring at the reflux temperature 9.4 g (79 mmol) of thionyl chloride in the course of 20 min and stirred in for 1 hour. Thereafter 12.9 g (97 mmol) of anhydrous aluminum chloride were metered in at room temperature in the course of 10 min and stirred in at 20°–25° C. for 30 min, and the mixture was worked up in a conventional manner to give 8.4 g of 2-fluoro-5H-dibenzo[a,d]cyclohepten-5-one in a 50% yield; melting point 119°–123° C.

We claim:

1. A process for preparing 5H-[a,d]cyclohepten-5-ones of the formula I

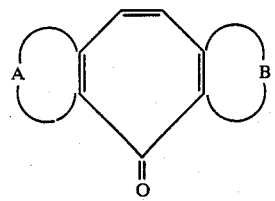

where radicals A and B are each radicals for completing a benzene ring, or a 1,2-naphthalene or a 2,3-naphthalene, each of which can be substituted 1 to 3 times by fluorine, chlorine, bromine, $CF_3$, $C_1$–$C_8$-alkyl or $C_1$–$C_8$-alkoxy, which comprises converting a (Z)-2-(2-arylethenyl)arylcarboxylic acid of the formula II

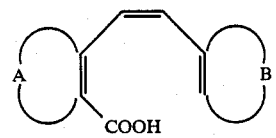

at from $-30°$ to $+120°$ C. with a halogenating agent for carboxylic acids into the corresponding carbonyl halide of the formula III

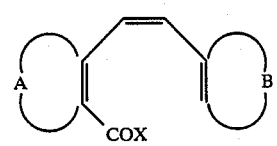

where X is halogen, and cyclizing the said carbonyl halide at from 0° to 100° C. in the presence of a Lewis acid.

2. A process as defined in claim 1, wherein an (E/Z)-isomer mixture of a 2-(2-arylethenyl)arylcarboxylic acid II is used.

3. A process as defined in claim 1, wherein the halogenating agent used is thionyl chloride, phosphorus oxychloride, phosphorus trichloride, phosphorus pentachloride, phosphorus tribromide or phosphorus pentabromide.

4. A process as defined in claim 1, wherein the halogenation is carried out at from 20° to 80° C.

5. A process as defined in claim 1, wherein the Lewis acid for the cyclization is aluminum chloride.

6. A process as defined in claim 1, wherein the cyclization is carried out at from 20° to 30° C.

7. A process as defined in claim 1, wherein the radicals A and B complete unsubstituted or substituted benzene rings.

8. A process as defined in claim 1, wherein the radicals A and B complete unsubstituted benzene rings.

* * * * *